United States Patent
Shalyt et al.

(10) Patent No.: US 7,879,222 B2
(45) Date of Patent: Feb. 1, 2011

(54) DETECTION OF ADDITIVE BREAKDOWN PRODUCTS IN ACID COPPER PLATING BATHS

(75) Inventors: Eugene Shalyt, Washington Township, NJ (US); Michael Pavlov, Fairlawn, NJ (US); Peter Bratin, Flushing, NY (US)

(73) Assignee: ECI Technology, Inc., Totowa, NJ (US)

( * ) Notice: Subject to any disclaimer, the term of this patent is extended or adjusted under 35 U.S.C. 154(b) by 810 days.

(21) Appl. No.: 11/895,836

(22) Filed: Aug. 27, 2007

(65) Prior Publication Data

US 2009/0057151 A1    Mar. 5, 2009

(51) Int. Cl.
    *G01N 27/26* (2006.01)
(52) U.S. Cl. .................... 205/775; 205/81; 204/434
(58) Field of Classification Search ............ 204/153.1, 204/434, 153; 205/81, 794, 794.5, 775; 427/8, 427/10
    See application file for complete search history.

(56) References Cited

U.S. PATENT DOCUMENTS

| | | | | |
|---|---|---|---|---|
| 4,479,852 A | * | 10/1984 | Bindra et al. | 205/81 |
| 5,192,403 A | * | 3/1993 | Chang et al. | 205/794.5 |
| 2001/0042694 A1 | * | 11/2001 | Robertson | 205/794 |
| 2003/0062266 A1 | * | 4/2003 | Chalyt et al. | 205/81 |
| 2004/0000484 A1 | * | 1/2004 | Sun et al. | 205/81 |
| 2004/0065561 A1 | * | 4/2004 | Chalyt et al. | 205/775 |
| 2005/0208201 A1 | * | 9/2005 | Kubota et al. | 427/8 |
| 2005/0247577 A1 | * | 11/2005 | Pavlov et al. | 205/794 |

OTHER PUBLICATIONS

Bratin et al. (Control of Damascene Copper Processes by Cyclic Voltammetric Stripping, 2001).*

* cited by examiner

*Primary Examiner*—Alexa D Neckel
*Assistant Examiner*—Jennifer Dieterle
(74) *Attorney, Agent, or Firm*—D. Morgan Tench

(57) ABSTRACT

An additive breakdown product in an acid copper plating bath sample is detected by performing a voltammetric analysis for the leveler additive in two measurement solutions comprising different volume fractions of the copper plating bath sample in a background electrolyte. When the plating bath sample contains a substantial concentration of the additive breakdown product, the analyses for the first and second measurement solutions indicate different concentrations for the leveler additive in the plating bath sample. A comparison of the leveler additive concentrations indicated by the two analyses provides a measure of the concentration of the additive breakdown product.

9 Claims, 2 Drawing Sheets

DETECTION OF ADDITIVE BREAKDOWN PRODUCTS IN ACID COPPER PLATING BATHS

BACKGROUND OF THE INVENTION

1. Field of the Invention

This invention is concerned with analysis of organic additives and contaminants in plating baths as a means of providing control over the deposit properties.

2. Description of the Related Art

Electroplating baths typically contain organic additives whose concentrations must be closely controlled in the low parts per million range in order to attain the desired deposit properties and morphology. One of the key functions of such additives is to level the deposit by suppressing the electrodeposition rate at protruding areas in the substrate surface and/or by accelerating the electrodeposition rate in recessed areas. Accelerated deposition may result from mass-transport-limited depletion of a suppressor additive species that is rapidly consumed in the electrodeposition process, or from accumulation of an accelerating species that is consumed with low efficiency. The most sensitive methods available for detecting leveling additives in plating baths involve electrochemical measurement of the metal electrodeposition rate under controlled hydrodynamic conditions for which the additive concentration in the vicinity of the electrode surface is well-defined.

Cyclic voltammetric stripping (CVS) analysis [D. Tench and C. Ogden, J. Electrochem. Soc. 125, 194 (1978)] is the most widely used bath additive control method and involves cycling the potential of an inert electrode (e.g., Pt) in the plating bath between fixed potential limits so that metal is alternately plated on and stripped from the electrode surface. Such potential cycling is designed to establish a steady state for the electrode surface so that reproducible results are obtained. Accumulation of organic films or other contaminants on the electrode surface can be avoided by periodically cycling the potential of the electrode in the plating solution without organic additives and, if necessary, polishing the electrode using a fine abrasive. Cyclic pulse voltammetric stripping (CPVS), also called cyclic step voltammetric stripping (CSVS), is a variation of the CVS method that employs discrete changes in potential during the analysis to condition the electrode so as to improve the measurement precision [D. Tench and J. White, J. Electrochem. Soc. 132, 831 (1985)]. A rotating disk electrode configuration is typically employed for both CVS and CPVS analysis to provide controlled hydrodynamic conditions.

For CVS and CPVS analyses, the metal deposition rate may be determined from the current or charge passed during metal electrodeposition but it is usually advantageous to measure the charge associated with anodic stripping of the metal from the electrode. A typical CVS/CPVS rate parameter is the stripping peak area ($A_r$) for a predetermined electrode rotation rate. The CVS method was first applied to control copper pyrophosphate baths (U.S. Pat. No. 4,132,605 to Tench and Ogden) but has since been adapted for control of a variety of other plating systems, including the acid copper sulfate baths that are widely used by the electronics industry [e.g., R. Haak, C. Ogden and D. Tench, Plating Surf. Fin. 68(4), 52 (1981) and Plating Surf. Fin. 69(3), 62 (1982)].

Acid copper sulfate electroplating baths require a minimum of two types of organic additives to provide deposits with satisfactory properties and good leveling characteristics. The suppressor additive (also called the "polymer", "carrier", or "wetter", depending on the bath supplier) is typically a polymeric organic species, e.g., high molecular weight polyethylene or polypropylene glycol, which adsorbs strongly on the copper cathode surface to form a film that sharply increases the overpotential for copper deposition. This prevents uncontrolled copper plating that would result in powdery or nodular deposits. An anti-suppressor additive (also called the "brightener", "accelerator" or simply the "additive", depending on the bath supplier) is required to counter the suppressive effect of the suppressor and provide the accelerated deposition within substrate recesses needed for leveling. Plating bath vendors typically provide additive solutions that may contain additives of more than one type, as well as other organic and inorganic addition agents. The suppressor additive may be comprised of more than one chemical species and generally involves a range of molecular weights.

Acid copper sulfate baths have functioned well for plating the relatively large surface pads, through-holes and vias found on printed wiring boards (PWB's) and have recently been adapted for plating fine trenches and vias in dielectric material on semiconductor chips. The electronics industry is transitioning from aluminum to copper as the basic metallization for semiconductor integrated circuits (IC's) in order to increase device switching speed and enhance electromigration resistance. The leading technology for fabricating copper IC chips is the "Damascene" process (see, e.g., P. C. Andricacos, Electrochem. Soc. Interface, Spring 1999, p. 32; U.S. Pat. No. 4,789,648 to Chow et al.; U.S. Pat. No. 5,209,817 to Ahmad et al.), which depends on copper electroplating to provide complete filling of the fine features involved. The organic additives in the bath must be closely controlled since they provide the copper deposition rate differential required for bottom-up filling.

As the feature size for the Damascene process shrank below 0.2 µm, it became desirable to utilize a third organic additive in the acid copper bath in order to avoid overplating the trenches and vias. Note that excess copper on Damascene plated wafers is typically removed by chemical mechanical polishing (CMP) but the copper layer must be uniform for the CMP process to be effective. The third additive is called the "leveler" (or "booster", depending on the bath supplier) and is typically an organic compound containing nitrogen or oxygen that also tends to decrease the copper plating rate. Leveler additive species tend to exert a relatively strong decelerating effect on the copper electrodeposition rate but are typically present in the plating bath at very low concentration so that their decelerating effect is weaker than that of suppressor additives. Due to their low concentration, leveler species tend to function under diffusion control.

In order to attain good bottom-up filling and avoid overplating of ultra-fine chip features, the concentrations of all three additives must be accurately analyzed and controlled. The suppressor, anti-suppressor and leveler concentrations in acid copper sulfate baths can all be determined by CVS analysis methods based on the effects that these additives exert on the copper electrodeposition rate. At the additive concentrations typically employed, the effect of the suppressor in reducing the copper deposition rate is usually much stronger than that of the leveler so that the concentration of the suppressor can be determined by the usual CVS response curve or dilution titration analysis [W. O. Freitag, C. Ogden, D. Tench and J. White, Plating Surf. Fin. 70(10), 55 (1983)]. Likewise, the anti-suppressor concentration can be determined by the linear approximation technique (LAT) or modified linear approximation technique (MLAT) described by R. Gluzman [Proc. 70$^{th}$ Am. Electroplaters Soc. Tech. Conf., Sur/Fin, Indianapolis, Ind. (June 1983)]. A method for measuring the leveler concentration in the presence of interference from both the suppressor and anti-suppressor is described in U.S. Pat. No. 6,572,753 to Chalyt et al.

For proper functioning of acid copper plating baths, it is also necessary to control the concentrations of additive breakdown products generated by electrochemical and/or chemical reactions involving additive species. Such additive breakdown products may degrade the properties of the copper deposit by interfering with the functioning of the additive system and/or by inclusion in the deposit. Depending on whether or not they exhibit activity similar to that of the parent additive, breakdown products could be considered auxiliary additives, which complicate control of the additive system, or contaminants, which directly degrade the deposit properties.

U.S. Pat. No. 6,749,739 to Chalyt et al. describes a CVS method for determining the relative concentrations of active suppressor additive species and suppressor breakdown contaminants in acid copper electroplating baths. In this method, the volume fraction of the plating bath added to the bath supporting electrolyte (or a background electrolyte) required to produce a predetermined decrease in the copper electrodeposition rate is determined for two predetermined copper deposition potentials or potential ranges. The volume fraction required for the more negative potential or potential range provides a measure of the concentration of the active suppressor additive since the suppressor breakdown contaminants are not effective at suppressing the copper deposition rate at the more negative potentials. The volume fraction required for the less negative potential or potential range provides a measure of the combined concentrations of the active suppressor additive and the suppressor breakdown contaminants. A comparison of the measured volume fractions for the two potentials or potential ranges yields the concentration of the suppressor breakdown contaminants relative to the active suppressor additive concentration.

U.S. patent application Ser. No. 10/883,803 to Chalyt et al. (filed May 4, 2004) describes a CVS method for analysis of anti-suppressor additive breakdown products that affect the metal electrodeposition rate and decompose as a function of time. In this method, a rate parameter for electrodeposition of the metal is measured at a plurality of times in the plating bath, or in a measurement solution comprising the plating bath. The concentration of the additive breakdown product in the plating bath, at a predetermined time, is determined from the slope of a plot of the metal electrodeposition rate parameter versus a time parameter, which provides a relative measure of the concentration of the additive breakdown product in the plating bath at the predetermined time. This method is useful for detecting the 3-mercaptopropylsulfonic acid (MPSA) breakdown product of the bis(sodiumsulfopropyl) disulfide (SPS) anti-suppressor additive in acid copper sulfate plating baths, for example.

No effective method for detecting leveler additive breakdown products in acid copper plating baths is currently available. A suitable method for detecting breakdown products of the leveler additive in acid copper plating baths is needed to avoid excessive concentrations of breakdown products that can degrade deposit properties, and to enable control of the leveler additive at the optimum level, which depends on the concentration of such breakdown products.

SUMMARY OF THE INVENTION

The present invention provides a method for determining the concentration of an additive breakdown product in a copper plating bath sample. The basic steps of the method comprise: performing a voltammetric analysis for a leveler additive in a first measurement solution comprising a background electrolyte and a first volume fraction of the copper plating bath sample, wherein a first value for a copper electrodeposition rate parameter is measured for the first measurement solution; repeating the voltammetric analysis for the leveler additive in a second measurement solution comprising a background electrolyte and a second volume fraction of the copper plating bath sample, wherein a second value for the copper electrodeposition rate parameter is measured for the second measurement solution; and comparing the first and second values measured for the copper electrodeposition rate parameter to determine the concentration of the additive breakdown product in the copper plating bath sample. The copper electrodeposition rate parameter reflects the rate of copper electrodeposition from the measurement solution under predetermined conditions.

When the concentration of the additive breakdown product in the plating bath sample is negligible, the first and second measurement solutions yield substantially the same concentration for the leveler additive in the plating bath sample. When the plating bath sample contains a substantial concentration of the additive breakdown product, the analyses for the first and second measurement solutions indicate different concentrations for the leveler additive in the plating bath sample. Typically, the measurement solution having the higher volume fraction of the plating bath sample indicates a higher concentration for the leveler additive. A comparison of the leveler additive concentrations indicated by the two analyses, which is an indirect comparison of the corresponding copper electrodeposition rate parameters, provides a measure of the concentration of the additive breakdown product in the plating bath sample.

Any suitable copper electrodeposition rate parameter measured by any suitable voltammetric analysis method may be used. A preferred copper electrodeposition rate parameter is the CVS copper stripping peak area ($A_r$) measured for a rotating platinum disk electrode cycled at a predetermined sweep rate between predetermined potential limits in the measurement solution. The copper electrodeposition rate parameter may be used directly to provide a relative measure of the concentration of the additive breakdown product, or may be used in conjunction with a calibration curve to provide an absolute or effective concentration of the additive breakdown product. In addition, the effect of the additive breakdown product on the measured voltammetric rate parameter may be taken into account, by mathematical extrapolation, for example, so as to provide a more accurate determination of the leveler additive concentration.

The present invention further provides an apparatus for automated application of the method of the invention. The apparatus comprises a computing device that is interfaced with suitable electronic and mechanical equipment, and includes a memory element with a stored algorithm for performing at least the basic steps of the method. The computing device may comprise a computer with integrated components, or may comprise separate components, a microprocessor and a memory device that includes the memory element, for example. The memory element may be of any suitable type, including computer hard drive, microprocessor chip, read-only memory (ROM) chip, programmable read-only memory (PROM) chip, magnetic storage device, computer disk (CD) and digital video disk (DVD), for example.

The present invention is useful for improving the quality of deposits from copper plating baths by providing a method and an apparatus for detecting additive breakdown products that may interfere with the functioning and analysis of leveler additives. The invention may be used to avoid excessive concentrations of breakdown products that can degrade deposit properties, and to enable control of the leveler additive at the optimum level, which depends on the concentration of such breakdown products. The method of the invention is especially useful for detection of breakdown products of leveler additives since a breakdown product and the parent additive tend to be chemically similar so as to exert similar effects on the copper electrodeposition rate parameter. Nonetheless, the method may also be used to detect breakdown products of other types of additives.

Further features and advantages of the invention will be apparent to those skilled in the art from the following detailed description, taken together with the accompanying drawings.

DETAILED DESCRIPTION OF THE INVENTION

Figure 1:
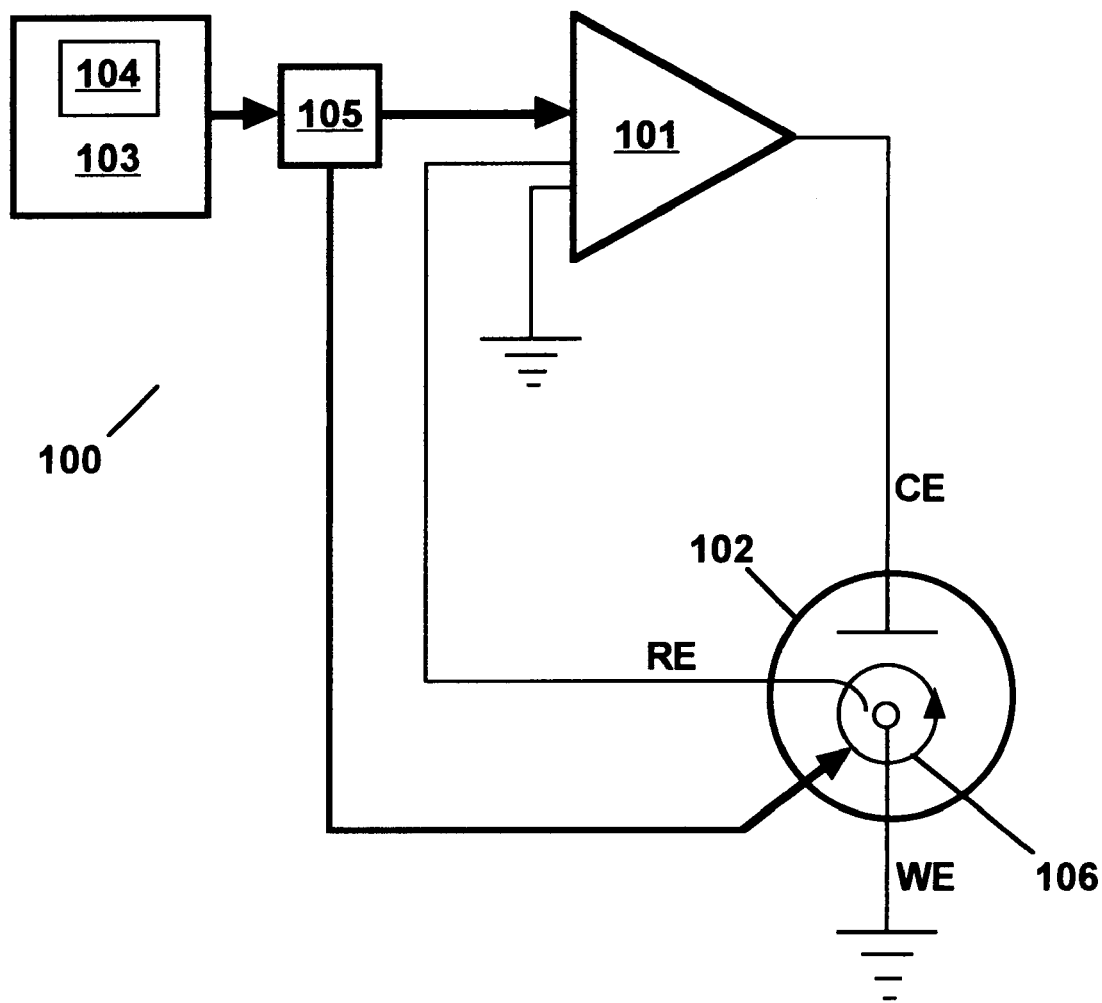
FIG. 1 is a schematic representation of a preferred apparatus of the invention.
Figure 2:
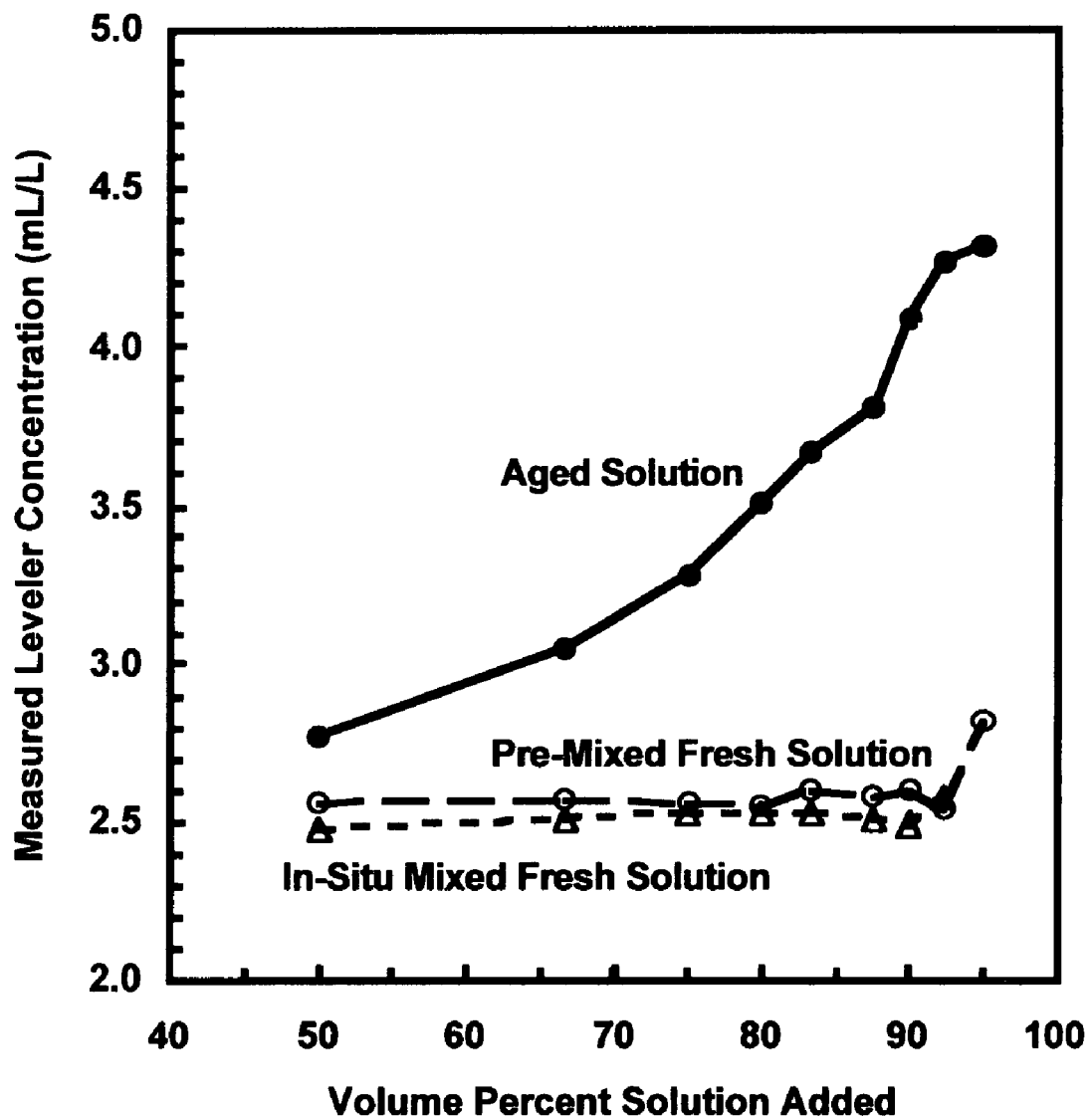
FIG. 2 shows plots of leveler additive concentration measured by CVS as a function of the volume percent of fresh acid copper sulfate plating solution (pre-mixed and in-situ mixed) and aged plating solution present in the CVS measurement solution. All of the plating solutions contained 2.5 mL/L of a leveler additive.

Technical terms used in this document are generally known to those skilled in the art. The term "electrode potential", or simply "potential", refers to the voltage occurring across a single electrode-electrolyte interface. In practice, the electrode potential often includes an appreciable resistive voltage drop in the electrolyte, which typically remains constant and does not affect voltammetric analysis results.

As used in this document, the terms "electroplating", "plating" and "electrodeposition" refer to copper electrodeposition and are equivalent. A "plating bath" is employed for practical copper plating and contains organic additives whose concentrations are controlled within ranges, whereas the corresponding "supporting electrolyte" typically has substantially the same inorganic composition as the plating bath but no organic additives. A "background electrolyte" comprises a supporting electrolyte containing one or more organic additives at predetermined concentrations. A preferred background electrolyte of the invention comprises a suppressor additive and an anti-suppressor additive at concentrations predetermined to be optimum for voltammetric analysis of the leveler additive, as described in U.S. Pat. No. 6,572,753 to Chalyt et al., which is assigned to the same assignee as the present application and is hereby incorporated by reference.

In this document, the term "standard addition" generally means addition of a predetermined quantity of a species (breakdown product or an additive, for example) to a predetermined volume of a solution (supporting electrolyte or a measurement solution, for example). The predetermined quantity may be a predetermined weight of the species or a predetermined volume of a standard solution containing the species. The symbol "M" means molar concentration. The "volume fraction" is the volume of a plating bath solution added to a background electrolyte divided by the total volume of the resulting solution. Calibration data are typically handled as calibration curves or plots but such data may be tabulated and used directly, especially by a computer, and the terms "curve" or "plot" include tabulated data.

The singular term "leveler additive breakdown product" is used to denote any breakdown product derived from the leveler additive employed in the plating bath but may encompass a plurality of chemical species. Furthermore, the leveler additive may contain a plurality of chemical species, and the leveler additive breakdown product may include chemical species derived from chemical or electrochemical reactions involving other additives, including suppressor and/or anti-suppressor additives. The term "additive breakdown product" encompasses leveler breakdown products and breakdown products of other additives, a suppressor additive, for example, that may be detected by the method of the invention.

Voltammetric data may be generated by scanning the electrode potential at a constant rate or by stepping the potential, or by a combination of potential scanning and stepping. A "cyclic voltammogram" is a plot of current or current density (on the y-axis) versus the working electrode potential (on the x-axis) typically obtained by cycling the working electrode potential with time between fixed negative and positive limits. A "potentiostat" is an electronic device for controlling the potential of a working electrode by passing current between the working electrode and a counter electrode so as to drive the working electrode to a desired potential relative to a reference electrode. Use of a potentiostat avoids passing appreciable current through the reference electrode, which might change its potential. Operation in the three-electrode mode may also reduce errors in the electrode potential associated with the resistive voltage drop in the electrolyte.

The present invention provides a method and an apparatus for determining the concentration of an additive breakdown product in a copper plating bath sample. The invention is suitable for analysis of acid copper plating baths comprising anions selected from the group consisting of sulfate, chloride, bromide, iodide, fluoroborate, sulfamate, alkylsulfonate, and mixtures thereof. The invention is especially suited to analysis of leveler additive breakdown products.

The method of the invention comprises the steps of: (1) performing a voltammetric analysis for a leveler additive in a first measurement solution comprising a background electrolyte and a first volume fraction of the copper plating bath sample, wherein a first value for a copper electrodeposition rate parameter is measured for the first measurement solution; (2) repeating the voltammetric analysis for the leveler additive in a second measurement solution comprising the background electrolyte and a second volume fraction of the copper plating bath sample, wherein a second value for the copper electrodeposition rate parameter is measured for the second measurement solution; and (3) comparing the first and second values measured for the copper electrodeposition rate parameter to determine the concentration of the additive breakdown product in the copper plating bath sample. These are the basic steps of the method. In a preferred embodiment, the background electrolyte contains a suppressor additive and an anti-suppressor additive at concentrations predetermined to be optimum for voltammetric analysis of the leveler additive in the copper plating bath sample.

The method of the invention may further comprise the steps of: (4) measuring the copper electrodeposition rate parameter for the background electrolyte to provide a baseline value for the copper electrodeposition rate parameter; and (5) normalizing the first and second values measured for the copper electrodeposition rate parameter relative to the baseline value for the copper electrodeposition rate parameter.

The method of the invention may further comprise the steps of: (6) generating a leveler additive calibration curve by performing the voltammetric analysis for the leveler additive in a plurality of leveler additive calibration solutions comprising the background electrolyte and known concentrations of the leveler additive, wherein values for the voltammetric rate parameter are measured for each of the leveler additive calibration solutions; and (7) comparing the first and second values measured for the copper electrodeposition rate parameter with the leveler additive calibration curve to determine the concentration of the additive breakdown product in the copper plating bath sample in terms of the leveler additive concentration.

The copper electrodeposition rate parameter of the invention is preferably measured via a cyclic voltammetric stripping (CVS) method. The CVS copper electrodeposition rate parameter is preferably selected from the group consisting of copper stripping peak area, copper stripping peak height, current at a predetermined cathodic potential, integrated current over a predetermined cathodic potential range, and average current over a predetermined cathodic potential range. A preferred copper electrodeposition rate parameter is a copper stripping peak area ($A_r$) for a rotating platinum disk electrode measured under predetermined conditions. The copper electrodeposition rate parameter of the invention may be measured by another method, an ac method, for example.

The apparatus of the invention comprises: (1) an electrochemical analysis system that includes a potentiostat, an electrochemical cell, a working electrode comprising a noble metal, a counter electrode, and a reference electrode; (2) a computing device having a memory element with a stored algorithm operative to effect at least the basic steps of the method of the invention, comprising (a) performing a voltammetric analysis for a leveler additive in a first measurement solution comprising a background electrolyte and a first volume fraction of the copper plating bath sample, wherein a first value for a copper electrodeposition rate parameter is measured for the first measurement solution, (b) repeating the voltammetric analysis for the leveler additive in a second measurement solution comprising the background electrolyte and a second volume fraction of the copper plating bath sample, wherein a second value for the copper electrodeposition rate parameter is measured for the second measurement solution, and (c) comparing the first and second values measured for the copper electrodeposition rate parameter to determine the concentration of the additive breakdown product in the copper plating bath sample; and (3) an interface enabling the computing device to control the electrochemical analysis system so as to perform at least the basic steps of the method of the invention. Suitable electrochemical analysis systems, computing devices, memory elements, and interfaces for use in the apparatus of the invention are well-known to those skilled in the art. In a preferred embodiment, the electrochemical analysis system of the apparatus of the invention further includes a rotation motor for rotating the working electrode.

The stored algorithm of the computing device of the invention may also be operative to effect additional steps of the method of the invention, comprising (d) measuring the copper electrodeposition rate parameter for the background electrolyte to provide a baseline value for the copper electrodeposition rate parameter, and (e) normalizing the first and second values measured for the copper electrodeposition rate parameter relative to the baseline value for the copper electrodeposition rate parameter.

The stored algorithm of the computing device of the invention may also be operative to effect additional steps of the method of the invention, comprising (f) generating a leveler additive calibration curve by performing the voltammetric analysis for the leveler additive in a plurality of leveler additive calibration solutions comprising the background electrolyte and known concentrations of the leveler additive, wherein values for the voltammetric rate parameter are measured for each of the leveler additive calibration solutions, and (g) comparing the first and second values measured for the copper electrodeposition rate parameter with the leveler additive calibration curve to determine the concentration of the additive breakdown product in the copper plating bath sample in terms of the leveler additive concentration.

FIG. 1 shows a schematic representation of a preferred apparatus 100 of the invention. An electronic potentiostat 101 is preferably used to control the potential of a working electrode WE by passing current between working electrode WE and a counter electrode CE so as to drive working electrode WE to a desired potential relative to a reference electrode RE. These three electrodes are immersed in a plating solution contained in electrochemical cell 102. Use of potentiostat 101 avoids passing appreciable current through reference electrode RE, which might change its potential. However, the invention may be practiced using any other suitable device for controlling the potential of working electrode WE. The tip of reference electrode RE, or an extension thereof, is preferably located as close as practical to working electrode WE so as to minimize errors in the working electrode potential associated with solution resistance. Most commercial potentiostats include a current follower device (not shown) to avoid errors in the potential of working electrode WE associated with the resistance of the current measuring device.

Preferred apparatus 100 of FIG. 1 also comprises a computing device 103 having a memory element 104 with a stored algorithm for effecting at least the basic steps of the invention, and an interface 105 enabling computing device 103 to control the electrochemical analysis system. Memory element 104 may be any one or a combination of available memory elements, including a computer hard drive, a microprocessor chip, a read-only memory (ROM) chip, a programmable read-only memory (PROM) chip, a magnetic storage device, a computer disk (CD) and a digital video disk (DVD), for example. Memory element 104 may be an integral part of computing device 103 or may be a separate device. Interface 105 may be an integral part of computing device 103 or may be a separate device.

As depicted in FIG. 1, preferred apparatus 100 preferably also comprises a rotation motor 106 for rotating working electrode WE, which preferably has a rotating disk configuration. Rotation motor 106 is preferably controlled by computing device 103, either directly or via interface 105 (as shown). Separate interface devices may also be used for the electrochemical analysis system and the rotation motor.

The copper deposition rate for the method of the invention is preferably determined by cyclic voltammetric stripping (CVS) or cyclic pulse voltammetric stripping (CPVS). As used in this document, the term "cyclic voltammetric stripping" or "CVS" implicitly includes the CPVS method, which is a variation of the CVS method. Likewise, the term "CVS rate parameter" includes the analogous CPVS voltammetric rate parameters.

In the CVS method, the potential of an inert working electrode, typically platinum, is cycled in a plating solution at a constant rate between fixed potential limits so that a copper is alternately electrodeposited on the electrode surface and anodically stripped back into the solution. Preferably, a rotating disk electrode configuration is used for the working electrode to control solution mass transport so as to improve the sensitivity and reproducibility of the analysis results. The copper deposition rate is preferably measured via the copper stripping peak area at a constant electrode rotation rate ($A_r$) but may also be determined from the stripping peak height, or from the electrode impedance, current (including average current), or integrated current (i.e., charge) measured for a predetermined cathodic potential or potential range (with or without electrode rotation). All of these rate parameters provide a relative measure of the copper electrodeposition rate that can readily be used for comparisons only when the measurement conditions are the same. Improved reproducibility and accuracy may be provided by using the normalized CVS rate parameter, $A_r/A_r(0)$, which is the ratio of the stripping peak area for the background electrolyte to that for the corresponding measurement solution.

For CVS analyses, a plurality of potential cycles is typically employed to condition the working electrode surface so as to provide reproducible results. In this case, data are accepted only when a steady-state condition is reached, as indicated by substantially equivalent voltammograms or voltammetric features on successive cycles. Typically, steady state is indicated by successive $A_r$ values that differ by less than a predetermined percentage (0.5%, for example).

The inert working electrode for CVS measurements may comprise any suitable electrically conducting material that is stable in the plating solution under the conditions used for the voltammetric analysis but preferably comprises a noble metal, for example, platinum, iridium, gold, osmium, palladium, rhenium, rhodium, ruthenium, and alloys thereof. Other oxidation-resistant metals and alloys, stainless steel, for example, might also be used as working electrode materials. A typical CVS rotating disk electrode is comprised of a platinum metal disk (3-5 mm diameter), with an electrical contact wire oil the backside, embedded flush with one end of an insulating plastic cylinder (10-20 mm diameter). The rotating disk electrode may be fabricated by press fitting the metal disk into a hole in the plastic but is preferably fabricated by hot pressing, which forms a seal between the metal and the plastic that prevents intrusion of the solution. A suitable plastic for mounting rotating disk electrodes by hot pressing is polytrifluorochloroethylene (Kel-F®). The rotating disk electrode is usually rotated at a constant rate (100-10,000 rpm) but the electrode rotation may be modulated with time.

Precise control over the working electrode potential needed for CVS measurements is typically provided via an electronic potentiostat in conjunction with a counter electrode and a reference electrode, e.g., silver-silver chloride (SSCE), mercury-mercury sulfate, or saturated calomel electrode (SCE). A double junction may be used to extend the life of the reference electrode by inhibiting intrusion of plating bath species. The counter electrode may be a reactive metal or an inert metal. Practically any electrical conductor that resists oxidation and reduction in the plating solution may be used as an inert counter electrode, including metals, alloys and conducting oxides. A preferred inert counter electrode material is 316 stainless steel, which is highly oxidation-resistant and relatively inexpensive, but other types of stainless steel or other oxidation-resistant alloys (Inconel, for example) may also be used. Other suitable inert counter electrode materials include noble metals, for example, platinum, iridium, gold, osmium, palladium, rhenium, rhodium, ruthenium, and alloys thereof.

Copper electrodeposition rates according to the invention may also be measured by methods other than CVS, including those based on measurements of the ac impedance of the cathode, for example. The same electrode materials and configurations can be used for such alternative methods. Although the precision and reproducibility of the analysis might be degraded, current measurements reflecting the copper deposition rate could also be made at a stationary electrode and/or without potential cycling. If a stationary working electrode is used for the additive breakdown product analysis of the invention, the hydrodynamic conditions at the electrode surface are preferably controlled, by stirring or pumping the solution, for example.

The composition of acid copper electroplating baths varies greatly depending on the type of bath and the supplier. High-acid baths typically contain 40-100 g/L copper sulfate, 140-240 g/L sulfuric acid and 25-100 ppm chloride ion. Low-acid baths typically contain 125-200 g/L copper sulfate, 1-40 g/L sulfuric acid and 25-100 ppm chloride ion. Acid copper plating bath additives are generally proprietary formulations supplied in the form of solutions that may contain more than one additive species or combination of additives. The chemical nature and concentrations of the additive species are typically not specified and may be changed from time to time by the supplier without notice.

Since chloride exerts a strong effect on the functioning of suppressor additives used in acid copper baths, its concentration should, if necessary, be adjusted to be within the appropriate range (typically, 25 to 100 ppm) in the plating bath sample being analyzed, and in the supporting electrolyte used for calibration. Variations in the chloride, sulfuric acid and copper ion concentrations within the ranges recommended by the bath supplier usually have a negligible effect on CVS analysis results.

Copper electrodeposition rate measurements are preferably made at a constant temperature (within $\pm 0.5°$ C.) since errors resulting from temperature variations may be significant. Acid copper baths are typically operated at ambient temperature but measurements may be made at a higher or a lower temperature. The accuracy of CVS rate parameter measurements may be improved by employing a slightly elevated solution temperature ($3°$ or $4°$ C. above room temperature, for example) that can be more consistently maintained. The effect of temperature on the additive decomposition rate should be taken into account. Copper deposition rate measurements for analysis and calibration solutions should be performed at the same temperature.

Best results for the analysis of the present invention are provided by optimizing the CVS measurement parameters for the particular bath type and additive system employed. The key CVS measurement parameters and their typical ranges for acid copper baths include the electrode rotation rate (100-10,000 rpm), potential scan rate (10-1000 mV/s), negative potential limit (−0.05 to −0.5 V vs. SSCE) and positive potential limit (1.4 to 1.8 V vs. SSCE). A positive potential limit of relatively high voltage (in the oxygen evolution region) is typically used so that organic species adsorbed on the electrode surface are removed by electrochemical oxidation on each cycle, which provides more reproducible results. Additional CPVS measurement parameters include the potentials and hold times for the pulses or steps used.

Optimization of the CVS measurement parameters typically involve variations in the negative potential limit and/or the potential scan rate, which determine the amount of copper deposited on the electrode and thus the sensitivity of the rate parameter. Another key optimization parameter is the electrode rotation rate, which determines the rate at which additive species and breakdown products are replenished at the electrode surface as they are consumed during copper electrodeposition. Typically, the rotation rate is increased for detection of a species present at relatively low concentration.

Description of a Preferred Embodiment

The background electrolyte used for the analysis of the invention preferably has substantially the same inorganic composition as the copper plating bath sample and contains suppressor and anti-suppressor additives at predetermined optimum concentrations.

In a preferred procedure, a calibration curve is generated by measuring $A_r(0)$ for the background electrolyte of the plating bath sample containing predetermined optimum concentrations of the suppressor and anti-suppressor additives, and measuring $A_r$ for each of a plurality of calibration solutions resulting from standard addition of the leveler additive to the background electrolyte. The preferred calibration curve is a plot of $A_r/A_r(0)$ as a function of the leveler additive concentration. For the breakdown product analysis, a first $A_r(0)$ is preferably measured for a first quantity of the background electrolyte just before adding a first predetermined volume fraction of the copper plating bath sample and measuring a first $A_r$ for the resulting first measurement solution. These measurements are then repeated by measuring a second $A_r(0)$ for a second quantity of the background electrolyte just before adding a second predetermined volume fraction of the copper plating bath sample and measuring a second $A_r$ for the resulting second measurement solution. Optionally, standard additions of the suppressor and anti-suppressor additives may be made to the copper plating bath sample to adjust the concentrations of these additives to the optimum values for the leveler analysis. The effective concentration of the additive breakdown product may then be determined by comparing the first and second $A_r/A_r(0)$ values measured for the first and second measurement solutions with the calibration curve.

In a preferred alternative procedure, the second measurement solution is produced by adding the second predetermined volume fraction of the copper plating bath sample to the first measurement solution. In this case, measurement of the second $A_r(0)$ value is unnecessary. This procedure also minimizes the analysis time and consumption of analytical reagents.

A preferred procedure for CVS voltammetric measurements is to cycle the potential of a rotating platinum disk electrode relative to a reference electrode between fixed positive and negative potential limits via a potentiostat and a counter electrode. Measurements are preferably made at a constant temperature (within $\pm 0.5°$ C.). The concentrations of inorganic components and organic additives in the plating bath are preferably maintained within the ranges recommended by the bath supplier.

Prior to the additive breakdown product analysis, the potential of the working electrode is preferably cycled (over the potential range used for the analysis) in the bath supporting electrolyte to condition the electrode surface. For both the electrode conditioning and the analysis, the potential of the working electrode is preferably cycled until successive $A_r$ values differ by less than a predetermined percentage (typically 0.5%).

The efficacy of the present invention was demonstrated via CVS analysis for the Viaform™ Leveler in the Low Acid Viaform™ (Enthone, Inc.) acid copper sulfate plating bath. The supporting electrolyte contained 160 g/L $CuSO_4 \cdot 5H_2O$, 10 g/L $H_2SO_4$, and 50 mg/L chloride ion. The background electrolyte comprised the supporting electrolyte and the suppressor and accelerator (anti-suppressor) additives at the optimum concentrations for the leveler analysis, as determined by the procedure described in U.S. Pat. No. 6,572,753 to Chalyt et al. Measurement solutions comprised copper plating bath samples diluted with 5-50 volume percent background electrolyte.

CVS measurements were made under potentiostatic control using a Qualilab QL-10® plating bath analyzer (ECI Technology, Inc.). The solution under analysis (50 mL) was contained in a polyethylene beaker cell (open to the atmosphere). The CVS rate parameter was the copper stripping peak area ($A_r$) measured using a 4-mm diameter platinum rotating disk electrode (3000 rpm) cycled at 50 mV/s between $-0.225$ V and $+1.575$ V vs. SSCE/M (silver-silver chloride electrode modified by replacing the solution in a standard SSCE electrode with a saturated AgCl solution also containing 0.1 M KCl and 10 volume % sulfuric acid). The counter electrode was a stainless steel rod (6 mm diameter). For $A_r$ measurements, the anodic current was integrated over the potential range from the zero-current potential (at the cathodic-anodic crossover) to 0.55 V vs. SSCE/M. During CVS measurements, the solution temperature was controlled in the range from 24 to 26° C.

Table 1 gives CVS leveler analysis results for measurement solutions comprising fresh plating solution (pre-mixed or mixed in-situ in the analysis cell) or aged plating solution added to background electrolyte at the specified volume percent. All of these solutions contained 2.5 mL/L of the Viaform™ leveler additive. Additions of either of the fresh plating solutions yielded $A_r/A_r(0)$ values that were practically independent of the volume percent of the solution added, as expected in the absence of additive breakdown products. Additions of the aged plating solution produced increasing $A_r/A_r(0)$ values, indicative of higher leveler concentrations, as the volume fraction of aged solution increased. In this case, the presence of leveler additive breakdown products in the aged plating solution produced an increase in the magnitude of the CVS copper deposition rate parameter. The increase in this parameter measured at a predetermined volume fraction of the plating bath sample provides a measure of the concentration of the leveler breakdown products in the plating bath sample.

TABLE 1

CVS Leveler Analysis Results for Measurement Solutions with Fresh Plating Solution (In-Situ Mixed and Pre-Mixed) or Aged Plating Solution Added

| Volume % Added | Measured Leveler Concentration (mL/L) | | |
|---|---|---|---|
| | Fresh In-Situ Mixed | Fresh Pre-Mixed | Aged Solution |
| 50.0 | 2.48 | 2.56 | 2.77 |
| 66.7 | 2.51 | 2.57 | 3.05 |
| 75.0 | 2.53 | 2.56 | 3.28 |
| 80.0 | 2.53 | 2.55 | 3.51 |
| 83.3 | 2.53 | 2.60 | 3.67 |
| 87.7 | 2.51 | 2.58 | 3.81 |
| 90.0 | 2.49 | 2.60 | 4.09 |
| 92.3 | 2.58 | 2.54 | 4.27 |
| 95.0 | | 2.82 | 4.32 |

FIG. 1 shows plots (same data as Table 1) of leveler additive concentration measured by CVS as a function of the volume percent of fresh acid copper sulfate plating solution (pre-mixed and in-situ mixed) and aged plating solution present in the CVS measurement solution. All of the plating solutions contained 2.5 mL/L of a leveler additive. The ostensible increase in the leveler concentration with increasing volume percent of the aged plating solution reflects the increased concentration of leveler additive breakdown products.

The preferred embodiments of the present invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

We claim:

1. A method for determining the concentration of an additive breakdown product in a copper plating bath sample, comprising the steps of:

performing a voltammetric analysis for a leveler additive in a first measurement solution comprising a background electrolyte and a first volume fraction of the copper plating bath sample, wherein a first value for a copper electrodeposition rate parameter is measured for the first measurement solution;

repeating the voltammetric analysis for the leveler additive in a second measurement solution comprising the background electrolyte and a second volume fraction of the copper plating bath sample, wherein a second value for the copper electrodeposition rate parameter is measured for the second measurement solution; and comparing the first and second values measured for the copper electrodeposition rate parameter to determine the concentration of the additive breakdown product in the copper plating bath sample.

2. The method of claim 1, further comprising the steps of:

measuring the copper electrodeposition rate parameter for the background electrolyte to provide a baseline value for the copper electrodeposition rate parameter; and normalizing the first and second values measured for the copper electrodeposition rate parameter relative to the baseline value for the copper electrodeposition rate parameter.

3. The method of claim 1, further comprising the steps of:

generating a leveler additive calibration curve by performing the voltammetric analysis for the leveler additive in a plurality of leveler additive calibration solutions comprising the background electrolyte and known concentrations of the leveler additive, wherein values for the voltammetric rate parameter are measured for each of the leveler additive calibration solutions; and comparing the first and second values measured for the copper electrodeposition rate parameter with the leveler additive calibration curve to determine the concentration of the additive breakdown product in the copper plating bath sample in terms of the leveler additive concentration.

4. The method of claim 1, wherein the copper plating bath sample comprises anions selected from the group consisting of sulfate, chloride, bromide, iodide, fluoroborate, sulfamate, alkylsulfonate, and mixtures thereof.

5. The method of claim 1, wherein the additive breakdown product comprises a leveler additive breakdown product.

6. The method of claim 1, wherein the background electrolyte contains a suppressor additive and an anti-suppressor additive at concentrations predetermined to be optimum for the voltammetric analysis for the leveler additive in the copper plating bath sample.

7. The method of claim 1, wherein the first and second values for the copper electrodeposition rate parameter are measured via an alternating current (ac) method.

8. The method of claim 1, wherein the first and second values for the copper electrodeposition rate parameter are measured via a cyclic voltammetric stripping (CVS) method and the copper electrodeposition rate parameter is selected from the group consisting of copper stripping peak area, copper stripping peak height, current at a predetermined cathodic potential, integrated current over a predetermined cathodic potential range, and average current over a predetermined cathodic potential range.

9. The method of claim 8, wherein the copper electrodeposition rate parameter is a copper stripping peak area ($A_r$) for a rotating platinum disk electrode measured under predetermined conditions.

* * * * *